(12) United States Patent
Modavis

(10) Patent No.: US 8,062,900 B2
(45) Date of Patent: Nov. 22, 2011

(54) OPTICALLY READABLE MICROPLATE

(75) Inventor: Robert A. Modavis, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 803 days.

(21) Appl. No.: 11/436,923

(22) Filed: May 17, 2006

(65) Prior Publication Data

US 2007/0154356 A1 Jul. 5, 2007

Related U.S. Application Data

(60) Provisional application No. 60/755,808, filed on Dec. 30, 2005.

(51) Int. Cl.
*G01N 21/00* (2006.01)

(52) U.S. Cl. ....... 436/164; 422/407; 422/52; 422/82.08; 422/82.09; 422/82.05; 422/82.11; 436/149; 436/172; 436/174; 436/518; 436/805; 436/809; 435/164; 435/165; 435/283.1; 435/287.1; 435/287.2; 435/4; 435/5; 435/7.2; 435/7.9; 204/403.01; 222/1; 359/321; 369/112.07; 382/133; 430/290; 430/321; 506/3; 506/39; 526/318.2; 526/319; 250/458.1; 250/559.29; 250/574; 356/128; 356/244; 356/246; 356/300; 356/326; 356/414; 356/416; 356/445; 385/12; 385/129; 385/130; 385/14; 385/37

(58) Field of Classification Search ............ 422/55, 422/82.05, 82.09, 102, 52, 82.08, 82.11, 422/99, 407; 435/7.9, 164, 165, 283.1, 287.1, 435/287.2, 4, 5, 7.2; 356/326, 128, 244, 356/246, 300, 414, 416, 445; 436/149, 164, 436/172, 174, 518, 805, 809; 204/403.01; 221/1; 359/321; 369/112.07; 382/133; 430/290, 430/321; 506/3, 39; 526/318.2, 319; 250/458.1, 250/559.29, 574; 385/12, 129, 130, 14, 37
See application file for complete search history.

(56) References Cited

U.S. PATENT DOCUMENTS

| | | | | |
|---|---|---|---|---|
| 4,815,843 | A | | 3/1989 | Tiefenthaler et al. ......... 356/128 |
| 5,307,144 | A | * | 4/1994 | Hiroshi et al. ................ 356/244 |
| 5,738,825 | A | | 4/1998 | Rudigier et al. .......... 422/82.11 |
| 2003/0059855 | A1 | * | 3/2003 | Cunningham et al. ......... 435/7.9 |
| 2004/0263841 | A1 | | 12/2004 | Caracci et al. ................ 356/300 |
| 2005/0099622 | A1 | | 5/2005 | Caracci et al. ................ 356/300 |
| 2005/0236554 | A1 | | 10/2005 | Fontaine et al. ........... 250/208.1 |

OTHER PUBLICATIONS

Oxford Dictionary Online, "Flush", Accessed online: http://www.askoxford.com/concise_oed/flush_2?view=uk.*

K. Tiefenthaler et al., "Integrated Optical Switches and Gas Sensors", Optics Letters, Apr. 1984, vol. 10, No. 4, pp. 137-139.

(Continued)

*Primary Examiner* — In Suk Bullock
*Assistant Examiner* — Dennis M White
(74) *Attorney, Agent, or Firm* — John L. Haack

(57) ABSTRACT

A microplate for use within an interrogation system and a method of using the microplate are disclosed. The microplate contains within the bottom of each well, an optical waveguide grating based sensor. Approximate to each sensor is a mask having an aperture of predetermined size. The aperture regulates the light that enters and exits the sensor upon successive scans and ensures repeatable readings from the sensor. In an extended embodiment, a method of detection is disclosed that utilizes a launch and receive system while employing the aforementioned microplate.

10 Claims, 8 Drawing Sheets

OTHER PUBLICATIONS

K. Tiefenthaler et al., "Sensitivity of Grating Couplers as Integrated-Optical Chemical Sensors", J. Opt. Soc. Am. B, vol. 6, No. 2, Feb. 1989, pp. 209-220.

C.E. Jordan et al., "Surface Plasmon Resonance Imaging Measurements of Electrostatic Biopolymer Adsorption onto Chemically Modified Gold Surfaces", Anal. Chem., 1997, vol. 69, pp. 1449-1456.

F. Morhard et al., "Immobilization of Antibodies in Micropatterns for Cell Detection by Optical Diffraction", Sensors and Actuators B, vol. 70, 2000, pp. 232-242.

* cited by examiner

OPTICALLY READABLE MICROPLATE

CROSS-REFERENCE TO RELATED APPLICATIONS

This application claims the benefit of U.S. Application Ser. No. 60/755,808 filed on Dec. 30, 2005 and entitled "Optically Readable Microplate" which is incorporated by reference herein in.

FIELD OF THE INVENTION

The present invention relates generally to a microplates and specifically to a microplate that is configured for the optical detection of its contents.

BACKGROUND OF THE INVENTION

The recent growth in many areas of biotechnology has increased the demand to perform a variety of studies, commonly referred to as assays, of biochemical systems. These assays include for example, biochemical reaction kinetics, DNA melting point determinations, DNA spectral shifts, DNA and protein concentration measurements, excitation/emission of fluorescent probes, enzyme activities, enzyme co-factor assays, homogeneous assays, drug metabolite assays, drug concentration assays, dispensing confirmation, volume confirmation, solvent concentration, and solvation concentration. Also, there are a number of assays which use intact living cells that require visual examination.

Assays of biochemical systems are carried out on a large scale in both industry and academia, so it is desirable to have an apparatus that allows these assays to be performed in a convenient and inexpensive fashion. Because they are relatively easy to handle, are low in cost, and generally disposable after a single use, multiwell plates are often used for such studies. Multiwell plates are typically formed from a polymeric material and consist of an ordered array of individual wells. Each well includes sidewalls and a bottom so that an aliquot of sample can be placed within each well. The wells may be arranged in a matrix of mutually perpendicular rows and columns. Common sizes for multiwell plates include matrices having dimensions of 8×12 (96 wells), 16×24 (384 wells), and 32×48 (1536 wells).

The materials used to construct a multiwell plate are selected based on the samples to be assayed and the analytical techniques to be used. For example, the materials of which the multiwell plate is made should be chemically inert to the components of the sample or any biological or chemical coating that has been applied to the multiwell plate. Further, the materials should be impervious to radiation or heating conditions to which the multiwell plate is exposed during the course of an experiment and should possess a sufficient rigidity for the application at hand.

In many applications, a transparent window in the bottom of each well is needed. Transparent bottoms are primarily used in assay techniques that rely on emission of light from a sample within the well and subsequent spectroscopic measurements. Examples of such techniques include liquid scintillation counting and techniques which measure light emitted by luminescent labels, such as bioluminescent or chemiluminescent labels, fluorescent labels, or absorbance labels. Optically transparent bottom wells also enable microscopic viewing of specimens and living cells within the well. Currently, optically transparent and ultraviolet transparent bottomed multiwell plates exist in the market and are used for the aforementioned purposes. These multiwell plates are typically made from a hybrid of different polymeric materials, one material making up the sidewalls of the wells and another material making up the bottom walls of the wells.

In other applications, detection of the binding of unlabeled molecular species is accomplished by determining changes in the overall refractive index of an optical system that employs a biosensor in the bottom of each well of the microplate. Typically, an optical waveguide grating (OWG) sensor comprises a substrate, a grating, a dielectric layer deposited on the grating and a biologically active region on the dielectric layer. When spectral light is launched into such a system, detecting changes in the wavelength of light that is reflected back (resonant wavelength) provides information on the interactions that are occurring in the biological layer. Likewise, should a single wavelength of light be directed into the system at a particular angle of incidence, changes in the angle that the light is reflected from the structure provides information on interactions occurring in the biological layer. The utility of assays performed in such systems relies on making successive analytical observations interplayed between steps in the assay. This way, a true "before and after" analysis may be accomplished revealing the occurrence (or absence) of biological or chemical molecular interactions. Therefore, the repeatable and consistent alignment and/or positioning of a microplate incorporated into or onto a stage for analytical interrogation has been a requirement for these systems.

Current measurement protocol requires five primary steps: (1) initial/background measurement, (2) removal of the plate (for additional assay steps), (3) reinsertion of the plate into the reader, (4) second measurement, and (5) comparison of first and second measurements. Following the placement of a microplate into an exact location, an initial measurement can be read by a photometric/optical instrument. Once the microplate is removed, and manipulation of its contents completed, examination of the microplate depends on the exact repositioning of the microplate into the reader. Therefore, the second/final measurement result can be adversely affected by the slightest change, rotational and/or translational, in microplate position between the initial and second/final measurement steps. Small, lateral displacements (e.g. ~1 micron) of the microplate (such as occur when the plate is removed and replaced) result in a spurious shift in the resonance wavelength. This arises since the small launch beam does not strike the same region of the grating during the initial measurement as it does during the final measurement and the fact that the grating resonance varies slightly with position. Accordingly, there is a need for a microplate design and method of analysis that will provide high levels of sensitivity while still allowing for slight lateral displacements within a detection system upon successive insertions into a reader. This need and other needs are satisfied by the multiwell plate and the method of the present invention.

SUMMARY OF THE INVENTION

One embodiment of the present device is a microplate having an array of wells disposed therein. Each well has formed within its bottom surface, a waveguide grating based biosensor. In order to properly control the light launched into the biosensor and/or received from the biosensor, a mask is located in proximity to the well bottom. An aperture in the mask allows for a predetermined amount or beam width of light to enter.

In another embodiment, a method is provided in which a launch system sends light into the sensor within a well of the microplate, a receive system receives light reflected back from the sensor and interrogates and records the received signal.

Further embodiments are provided within the detailed description.

BRIEF DESCRIPTION OF THE DRAWINGS

The invention is best understood from the following detailed description when read with the accompanying drawing figures. It is emphasized that the various features are not necessarily drawn to scale. The dimensions may be arbitrarily increased or decreased for clarity of discussion.

DETAILED DESCRIPTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Figure 1:
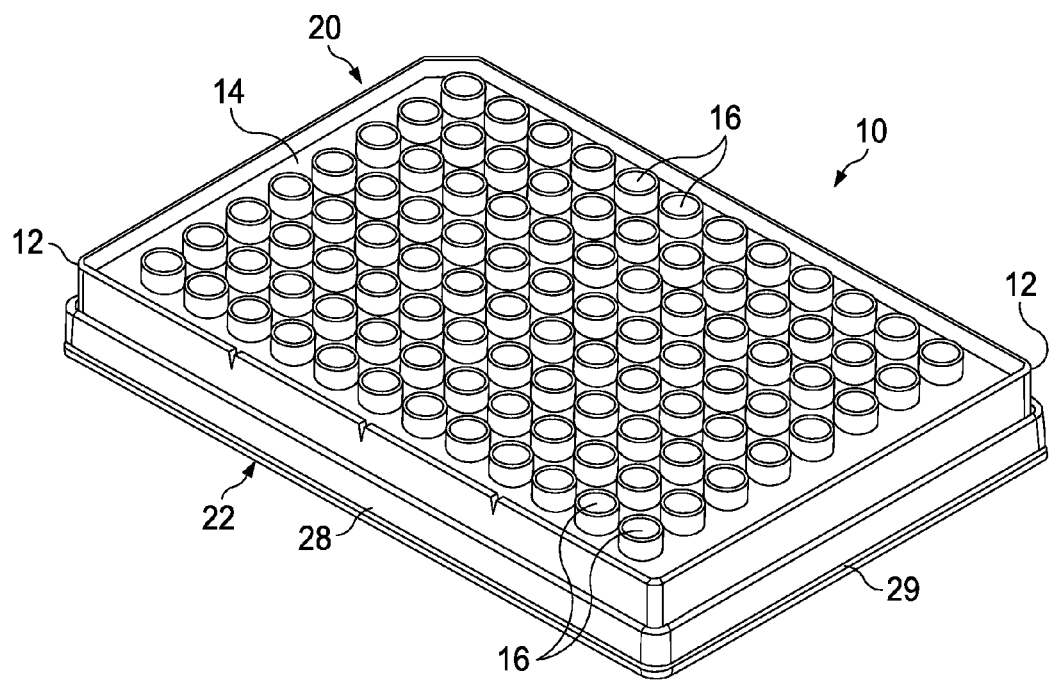
FIG. 1 is a perspective view of a prior art microplate

Referring to FIG. 1, there is illustrated a perspective view of an exemplary multiwell plate 10. The multiwell plate 10 (e.g., microplate) includes a peripheral skirt 12 and a top surface 14 having an array of wells 16 each of which is capable of receiving an aliquot of sample to be assayed. Preferably, the multiwell plate 10 conforms to industry standards for multiwell plates; that is to say, the multiwell plate 10 is bordered by a peripheral skirt 12, laid out with ninety-six wells 16 in an 8×12 matrix (mutually perpendicular 8 and 12 well rows). In addition, the height, length, and width of the multiwell plate 10 preferably conform to industry standards. However, the present invention can be implemented in a multiwell plate that has any number of wells and is not limited to any specific dimensions and configurations.

Optical-based biosensors generally consist of two components: a highly specific recognition element and an optical transducer that converts the molecular recognition event into a quantifiable signal. Direct surface sensing methods include surface plasmon resonance (SPR) (Jordan & Corn, Anal. Chem., 1997, 69:1449-1456), grating couplers (Morhard et al., Sensors and Actuators B, 2000, 70, 232-242), ellipsometry (Jin et al., Analytical Biochemistry, 1995, 232, 69-72), evanescent wave devices (Huber et al., Sensors and Actuators B, 1992, 6, 122-126), and reflectometry (Brecht & Gauglitz, Biosensors and Bioelectronics, 1995, 10, 923-936). The instrumentation typically used to interrogate SPR or waveguide grating sensors utilizes an optical beam with the appropriate spectral or angular content, such that when this beam is reflected by the sensing surface, the resonant angle or wavelength response becomes dominant in the output response. A common feature is that both SPR and grating coupler (i.e., OWG or RWG) technologies are sensitive to refractive index changes at/near the sensor surface.

One major application of this technology as a biosensor is to monitor in situ the interfacial behaviors of specific analytes under the conditions of different surface properties and different solution characteristics. This technology allows label free detection, unlike most of the current technologies which requires specific labels for readout of the interaction signals. The disadvantages associated with the labeling is that labeling is not only labor-intensive and costly, but also has potential to create interference with the biological properties of target biologicals or compounds such that the data interpretation would be difficult and false information might be generated from assays.

Figure 2:
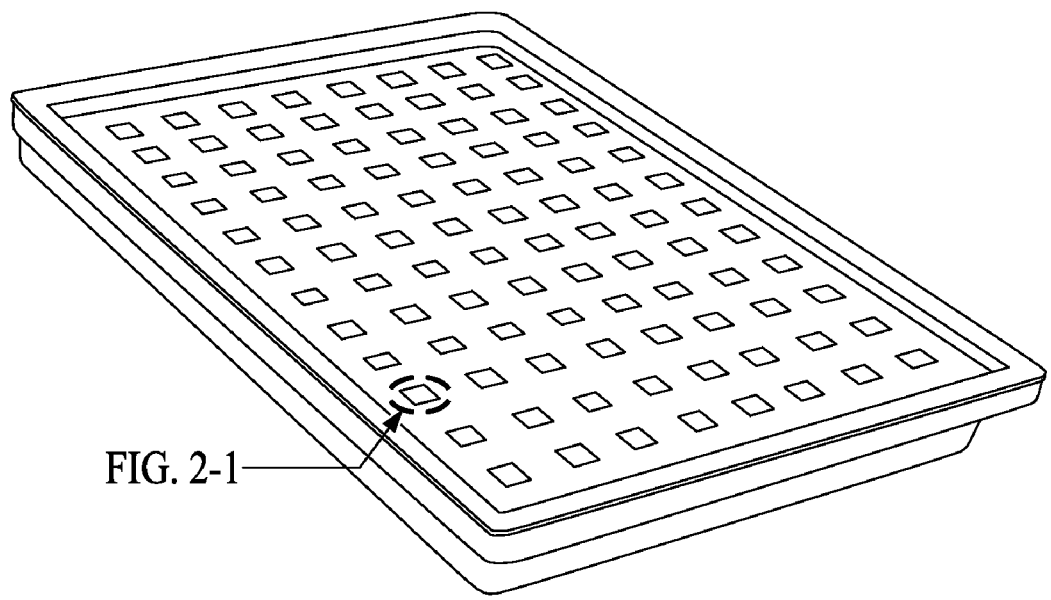
FIG. 2 is a perspective bottom view of a prior art microplate
Figures 1, 2:
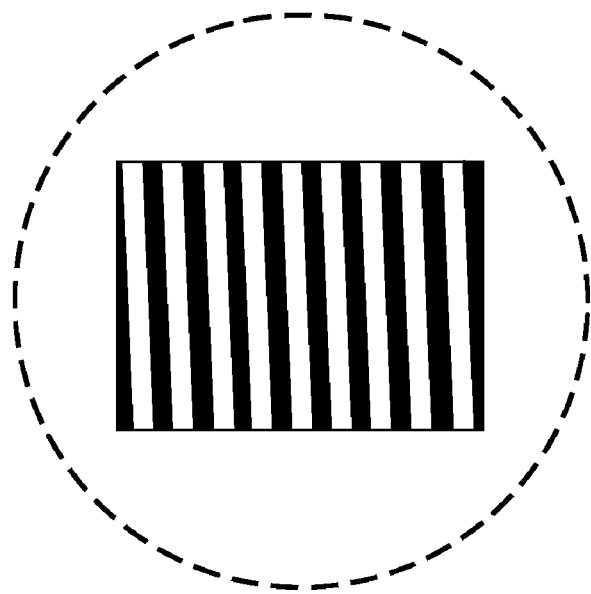
Figure 2A:
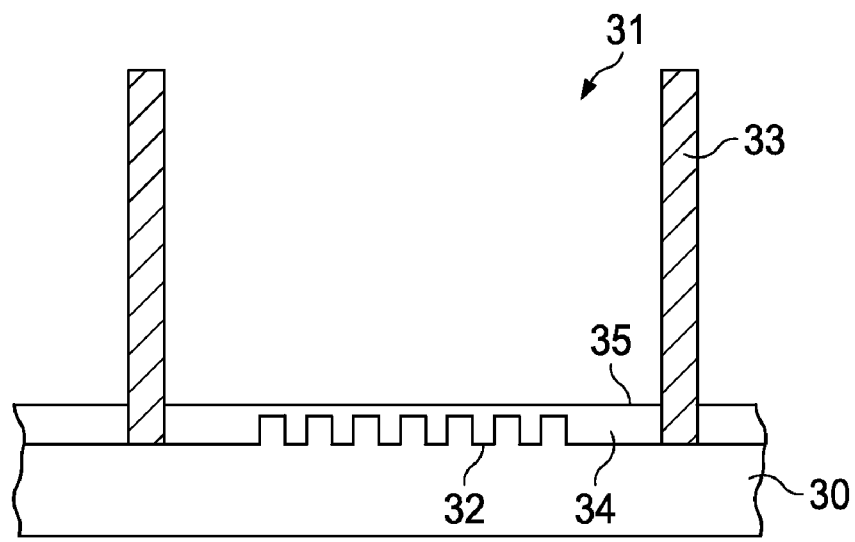
FIG. 2A is a partial cross sectional view of a well of the plate of FIG. 2.

Referring to FIG. 2 and FIG. 2A, is a microplate containing specific OWG biosensors at the bottom of each well within the plate. The inset in FIG. 2 is a scanning electronic microscopic image showing the structure and dimension of the grating. The white bar represents one micron. As disclosed herein, the label free biosensors, such as a RWG or OWG biosensor can be used in conjunction with this invention. FIG. 2A demonstrates an OWG sensor in the bottom of a single well of a plate. The OWG sensor is made up of a substrate 30, a grating 32, and a waveguide layer 34. The waveguide layer 34 has a refractive index higher than that of the substrate 30. The well 31 is defined by walls 33 and a bottom 35. The instrumentation typically used to interrogate SPR or waveguide grating sensors utilizes an optical beam with an appropriate spectral or angular content, such that when this beam is reflected by the sensing surface, the resonant angle or wavelength response becomes dominant in the output beam. The waveguide-based biosensors can be used to detect changes in the media surrounding the waveguide as the eletromagnetic field propagating in the waveguide will extend into the surrounding media as an evanescent eletromagnetic field (the depth is referred to the penetration depth or sensing volume). When mass redistribution occurs within the sensing volume, a response change is observed as an angular or spectral change in the reflected beam. Resonant waveguide grating sensors (RWG) and optical waveguide grating sensors (OWG) can be used interchangeably. The RWG biosensor is an evanescent-wave sensor, based on the resonant coupling of light into a waveguide by means of a diffraction grating. The RWG-based surface sensing technology takes advantage of the evanescent field, which penetrates less than a wavelength out of the waveguide surface, to selectively respond to the adsorption of immobilized chemical and biological molecules over a given spectral bandwidth.

An example of an optical LID biosensor is a SPR sensor or a waveguide grating based sensor. Other optical-based biosensors can also be used such as ellipsometry devices, evanescent wave devices, and reflectometry devices. For a more detailed discussion about the structure and operation of these two types of optical LID biosensors are provided in U.S. Pat. No. 4,815,843 entitled "Optical Sensor for Selective Detection of Substances and/or for the Detection of Refractive Index Changes in Gaseous, Liquid, Solid and Porous Samples" and K. Tiefenthaler et al. "Integrated Optical Switches and Gas Sensors" Opt. Lett. 10, No. 4, April 1984, pp. 137-139, which are both herein incorporated in their entireties at least for material related to biosensors. In particular, optical biosensors disclosed in U.S. patent application Ser. No. 10/602,304, filed Jun. 24, 2003 having publication no. US-2004-0263841, published Dec. 30, 2004 and U.S. patent application Ser. No. 11/019,439, filed Dec. 21, 2004, and United States Patent App. For "OPTICAL INTERROGATION SYSTEM AND METHOD FOR 2-D SENSOR ARRAYS" by Norman H. Fontaine, Eric J. Mozdy, and Po Ki Yuen, filed on Mar. 31, 2005, all of which are herein incorporated in their entireties by reference but at least for biosensors and their uses.

An example of a symmetry waveguide grating biosensor is a grating coupler or coupled biosensors. Examples of grating coupled biosensors can be found in Jordan & Corn, "Surface Plasmon Resonance Imaging Measurements of Electrostatic Biopolymer Adsorption onto Chemically Modified Gold Surfaces," Anal. Chem., 1997, 69:1449-1456; Morhard et al., "Immobilization of antibodies in micropatterns for cell detection by optical diffraction," Sensors and Actuators B, 2000, 70, 232-242; and Tiefenthaler, K., and W. Lukosz, "Sensitivity of grating couplers as integrated optical chemical sensors" J. Opt. Soc. Am. B, 1989, 6, 209-220 and are herein incorporated by reference in their entireties but at least for material related to grating coupled biosensors.

Figure 2B:
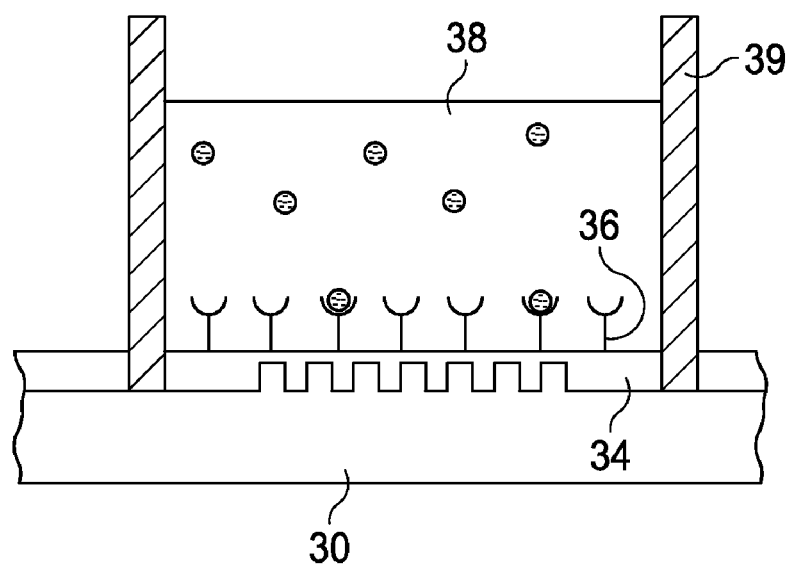
FIG. 2B is a partial cross sectional view of a well of the plate of FIG. 2 in use as an optical biosensor.

Grating coupler biosensors are evanescent-wave sensors based on the resonant coupling of light into a waveguide by means of a diffraction grating. The grating coupler sensor consists of the combination of a waveguide and diffraction grating. FIG. 2B shows a classical four layer waveguide biosensor consisting of a thin film of a high refractive index (e.g., $n_F \sim 2.36$ for $Nb_2O_5$) material 34 with a thickness of $d_F$ on a substrate 30 of lower index (e.g., $n_s \sim 1.50$ for 1737 glass). Immobilized on the waveguide film is an adlayer of biologicals 36 with a refractive index ($n_A$) around 1.4 and a thickness $d_A$, and on top of the entire sensor structure is the cover medium 38, being the biological solution with index ($n_c$) around 1.35. In this conventional configuration, the refractive index of the waveguide thin film 34 is at least 1% higher than that of the substrate 30 of lower index, for example, by 1%, 5%, 10%, 20%, 30%, 50%, 70%, or 100%. The refractive index of the substrate of lower index is higher than that of the cover medium, for example, by 5%, 7%, 10%, 15%, 20%, 30%, or 50%. The refractive index of the cover medium, generally aqueous medium for most assay applications, is typically around 1.32, 1.35, and 1.38.

The guided waves or modes in planar waveguide are $TE_m$ (transverse electric or s-polarized) and $TM_m$, (transverse magnetic or p-polarized), where m=0, 1, 2, . . . is the mode number. A given guided mode refers to, for example, $TM_0$, $TE_0$, $TM_1$, $TE_1$, etc. A laser illuminates the waveguide at varying angles and light is coupled into the waveguide only at specific angles determined by both the effective refractive index of the guided mode, denoted as N, and the grating period. Since the evanescent tails of the light mode propagates in the substrate and cover media but still along the film, the light modes experience or sense all three media at the same time. It means that the refractive index experienced by the traveling light modes is a weighed mixture of the three refractive indices. The effective refractive index N can be calculated numerically from the mode equation, which can be written in the following form for a four layer waveguide assuming that the thickness of the thin adlayer is less than the wavelength of the light ($d_A \ll \lambda$) [Tiefenthaler, K., and W. Lukosz, "Sensitivity of grating couplers as integrated optical chemical sensors" J. Opt. Soc. Am. B, 1989, 6, 209-220]:

$$0 \cong \pi m - k(n_F^2 - N^2)^{0.5} \qquad (1)$$
$$\left(d_F + d_A \frac{n_A^2 - n_C^2}{n_F^2 - n_C^2}\left[\frac{(N/n_C)^2 + (N/n_A)^2 - 1}{(N/n_C)^2 + (N/n_F)^2 - 1}\right]^\sigma\right) +$$
$$\arctan\left[\left(\frac{n_F}{n_S}\right)^{2\sigma}\left(\frac{N^2 - n_S^2}{n_F^2 - N^2}\right)^{0.5}\right] +$$
$$\arctan\left[\left(\frac{n_F}{n_C}\right)^{2\sigma}\left(\frac{N^2 - n_C^2}{n_F^2 - N^2}\right)^{0.5}\right]$$

Here, $k=2\pi/\lambda$, where $\lambda$ is the vacuum wavelength of the guided light. $\sigma$ is a mode type number which equals 1 for TE and 0 for TM modes.

If light is coupled into the waveguide by a surface-relief grating, N can be calculated from the incoupling angle:

$$(\pm)N = N_{air}\sin(\theta) + l\lambda/\Lambda \qquad (2)$$

Where $N_{air}=1.0003$ is the refractive index of air, $\theta$ the angle of incidence measured in air, $\lambda$ the wavelength, $\Lambda$ the grating period and $l=\pm 1, \pm 2, \ldots$ the diffraction order. The plus and minus signs on the left side of this equation hold for guided modes propagating in the +x and −x directions, respectively.

The induced effective refractive index change $\Delta N$ in the waveguide in the grating area lead to changes $\Delta\theta$ as described in the following equation:

$$\Delta N = n_{air}\cos(\theta)\Delta\theta \qquad (3)$$

Since the laser light is coupled to and propagates parallel to the surface in the plane of a waveguide film, this creates an electromagnetic field (i.e., an evanescent wave) in the liquid adjacent to the interface. The amplitude (Em) of the evanescent wave decays exponentially with increasing distance d from the interface:

$$E_m(d) = E_m(0)\exp\left(\frac{-d}{\Delta Z_C}\right) \qquad (4)$$

with $$\Delta Z_C = \frac{1-\sigma}{k(N^2 - n_C^2)^{0.5}} + \frac{\sigma[(N/n_F)^2 + (N/n_C)^2 - 1]^{-1}}{k(N^2 - n_C^2)^{0.5}} \qquad (5)$$

is the penetration depth of the waveguide mode with high intensity into the cover medium.

A given mode type propagates as a guided wave if two conditions are fulfilled: (a) the refractive index of the waveguide film has to be larger than the surrounding substrate and cover medium refractive indices; and (2) the thickness of the waveguide film is larger than a well-defined value, call the cut-off thickness $d_c$:

$$d_C = \frac{1}{k(N_F^2 - n_{max}^2)^{0.5}}\left(\pi m + \arctan\left(\left(\frac{n_F}{n_{min}}\right)^{2\sigma}\left(\frac{n_{max}^2 - n_{min}^2}{n_F^2 - n_{max}^2}\right)^{0.5}\right)\right) \qquad (6)$$

Where $n_{min}=\min\{n_s,n_c\}$ and $n=\max\{n_s,n_c\}$. It is known that when the film thickness approaches the cut-off thickness, the effective refractive index, N, of the mode approaches $n_{max}$. Furthermore, equation 5 implies that the penetration depth goes to infinity at the cut-off point on the side of the film that has the bigger refractive index, which the penetration depth will be finite on the other side. The $d_{eff}$ will be also infinite in this case.

Again, the exponentially decaying evanescent field from light propagating in waveguide sensors only penetrates the cover medium to a depth of 50-200 nm with high intensity, when the waveguide grating biosensors fall into the conventional waveguide configuration. This value is dependent upon the refractive indices of the media present at the interface, the illumination wavelength as well as the grating structure. When the incident angle equals the critical value, $d_c$ goes to infinity, and the wavefronts of refracted light are normal to the surface.

In certain embodiments, the optical detection system can be either angular interrogation, or wavelength interrogation, or their variation systems, for example, the arrayed angular interrogation system or the scanning wavelength interrogation system (U.S. application Ser. No. 10/993,565, filed Nov. 18, 2004 by Norman H. Fontaine, Prantik Mazumder, Eric J. Mozdy, Mark A. Quesada, Po Ki Yuen and "METHOD FOR ELIMINATING CROSSTALK BETWEEN WAVEGUIDE GRATING-BASED BIOSENSORS LOCATED IN A MICROPLATE AND THE RESULTING MICROPLATE" by Ye Fang, Ann M. Ferrie, Norman H. Fontaine, Anthony G. Frutos, Eric J. Mozdy, ChuanChe Wang, and Po Ki Yuen filed on Mar. 31, 2005 (Both of which are incorporated in their entireties and at least for material related to biosensors, scanning devices, and microplates), when optical waveguide biosensors are used. U.S. patent application Ser. No. 10/602,304, filed Jun. 24, 2003 having publication no. US-2004-0263841, published Dec. 30, 2004 and U.S. patent application Ser. No. 11/019,439, filed Dec. 21, 2004, and United States Patent App. For "OPTICAL INTERROGATION SYSTEM AND METHOD FOR 2-D SENSOR ARRAYS" by Norman H. Fontaine, Eric J. Mozdy, and Po Ki Yuen, filed on Mar. 31, 2005, all of which are herein incorporated in their entireties by reference but at least for biosensors and their uses.

Because the evanescent field of the guided mode projects into the cover liquid, the waveguide mode is exquisitely sensitive to the cover environment. When binding events occur at the waveguide surface (e.g., interactions between biological or chemical materials), the result is a change in the index of the cover medium because of the change of mass, the propagation constant of the waveguide mode must also change in accordance with Maxwell's electromagnetic equations. As a result of the phase-matching condition for the waveguide grating structure mentioned above, the preferred coupling angle (or wavelength) of input light must change in accordance with the waveguide propagation constant change. The preferred coupling angle (or wavelength) is monitored closely for these changes. In either event and in order to be most useful, the launch beam must strike the same region of the grating during the initial measurement as it does in each successive measurement.

Figure 3:
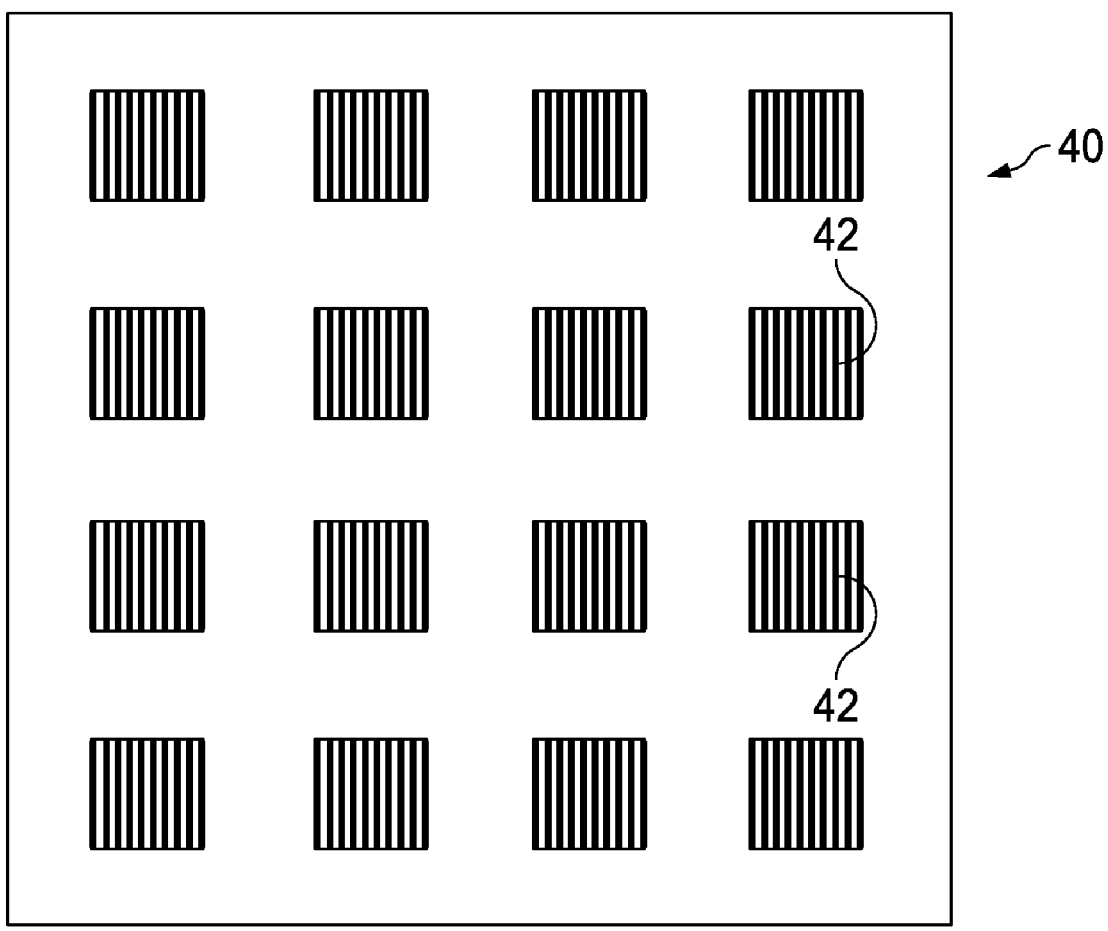
FIG. 3 is a bottom view of a prior art microplate
Figure 4:
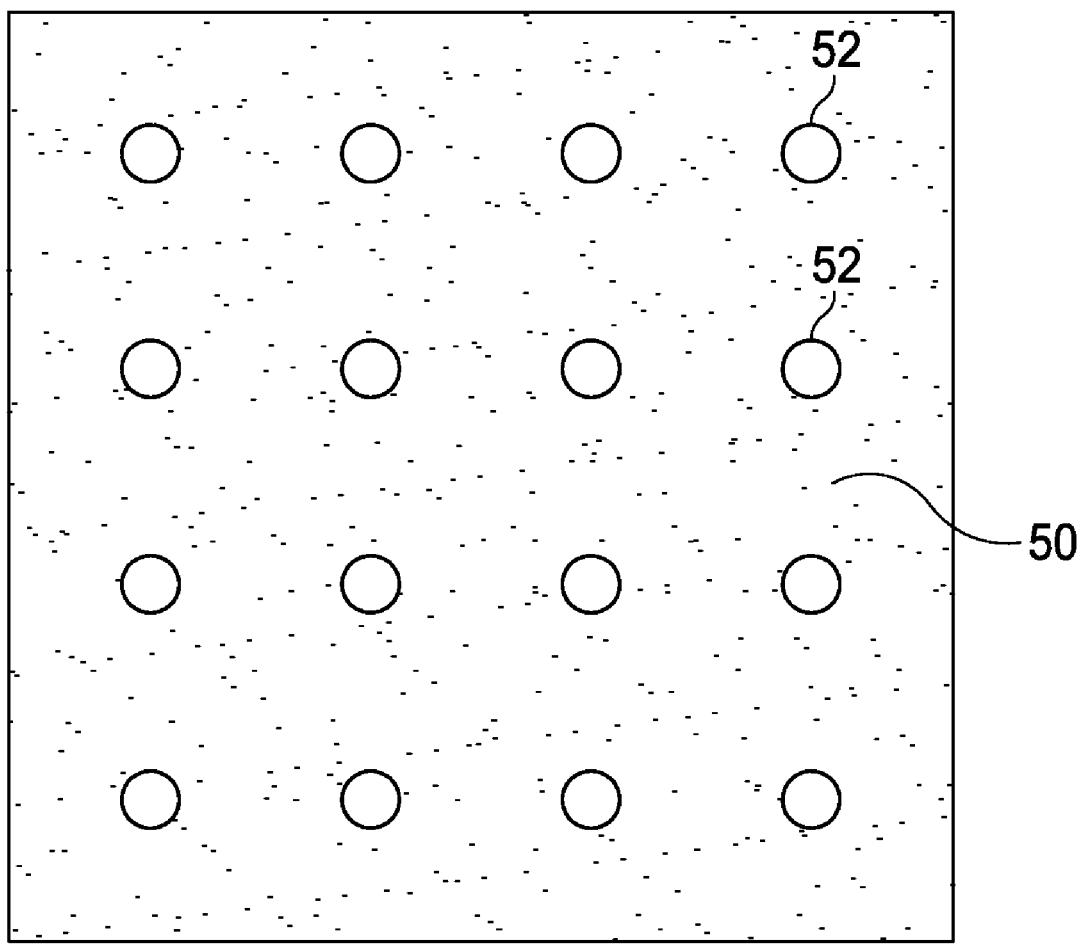
FIG. 4 is a top view of the aperture mask of the present invention.
Figure 5A:
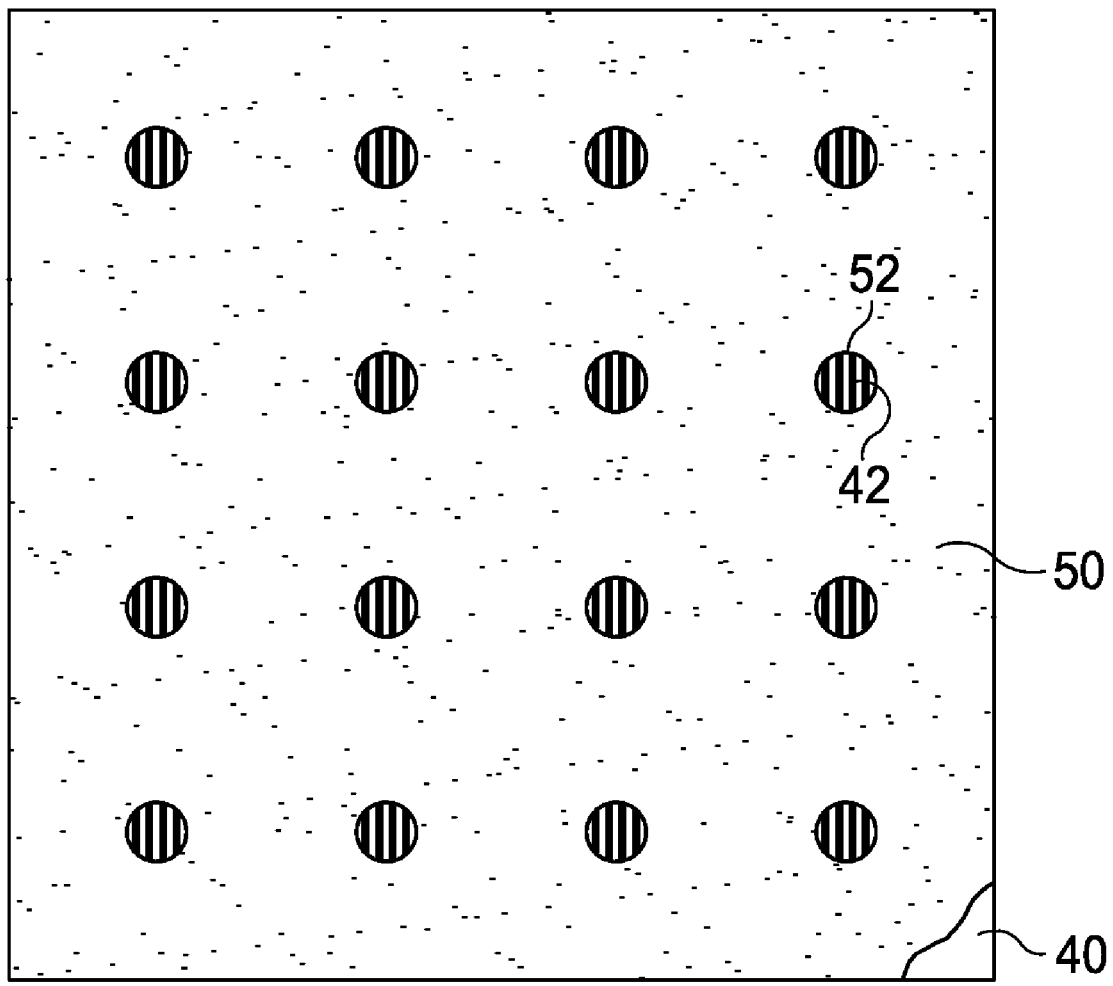
FIG. 5A is a bottom view of the microplate of the present invention.
Figure 5B:
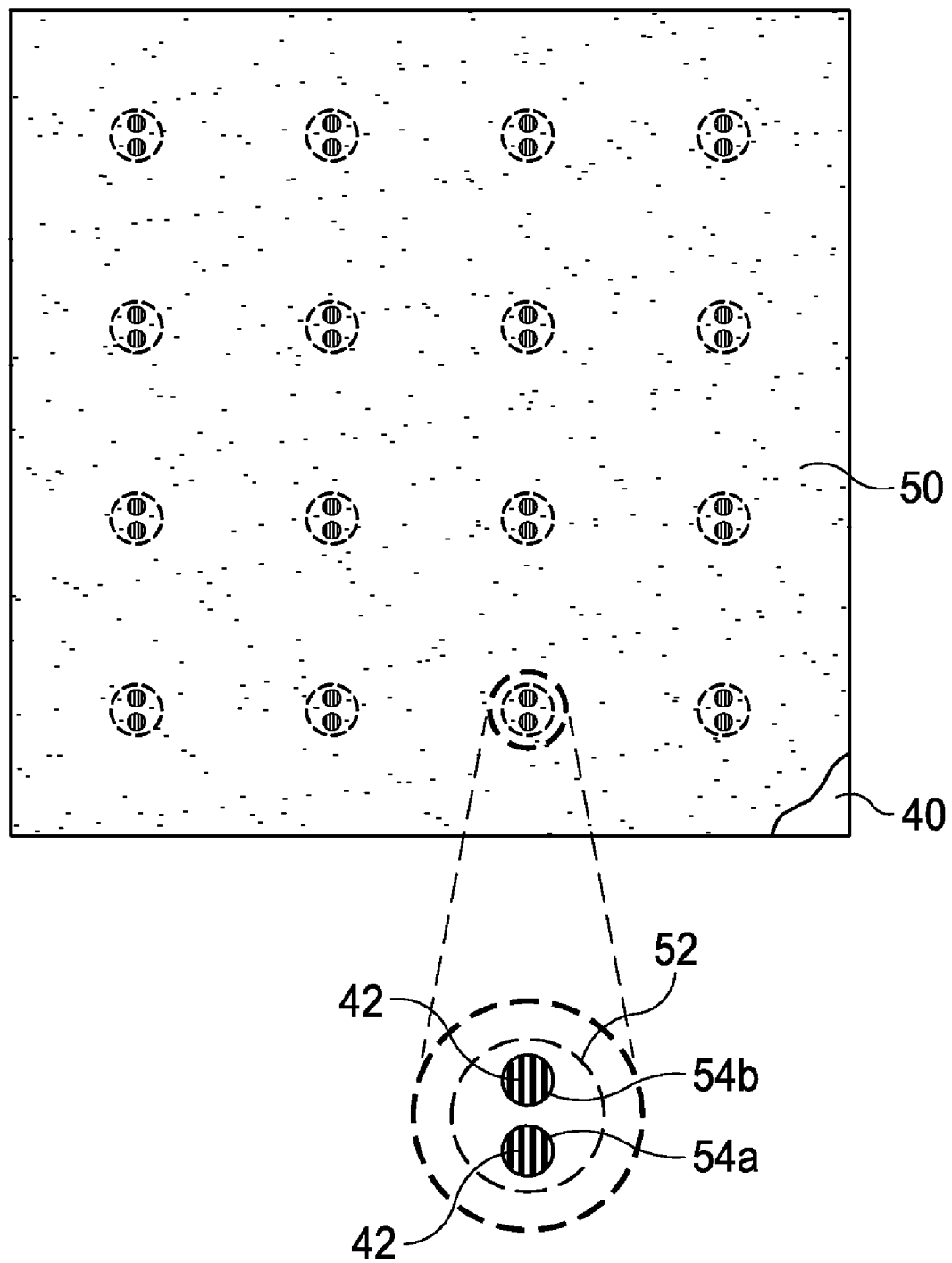
FIG. 5B is a bottom view of the microplate in accordance with another embodiment of the present invention.

By using an aperture at the bottom surface of each well of the microplate, one may be assured that the same region is indeed struck. The size of this aperture 52 is smaller than the grating sensor and the launch beam is constructed so that the amplitude and phase of the beam is as uniform as possible within the aperture. This can be accomplished, for example, by overfilling the aperture with a large Gaussian beam. If the beam width is large compared with the diameter of the aperture, then the amplitude and phase of the beam will be nearly uniform over (and a little beyond) the extent of the aperture. This aperture limits the size of the launch beam and, since the aperture is attached to the microplate, also ensures that the light that passes through it will always hit the same region of the grating, even if the microplate is shifted slightly. Since the beam (which is fixed in space) is nearly uniform, the illumination which is transmitted through the shifted aperture will be nearly the same as that transmitted by the unshifted aperture. Therefore, the shift in the grating resonance caused by a shift in the microplate is minimized. Several aperture shapes are possible, including circular, oval or even a pair of circular apertures (see FIG. 5B). In one embodiment that utilizes a 96-well plate format, the size of the aperture is 1-2 mm in diameter. FIG. 3 shows a bottom surface of a lower plate of a microplate. For illustrative purposes, a series of gratings 42 are arrayed in a 4×4 matrix on one surface of the substrate. Any number of gratings in any array format (such as a 12×8, 96 well format) may be employed. FIG. 4 illustrates a mask having an array of apertures that align with the grating array 42 of the substrate 40 of FIG. 3. FIG. 5A shows the mask 50 after having been bonded to the substrate 40. Each aperture is sized identically. FIG. 5B shows an example of the mask 50 bonded to the substrate 40 having an array of paired apertures 54a and 54b rather than a single aperture 52 of FIG. 5a. Each pair of apertures 54a and 54b aligns with a single grating 42.

Figure 6:
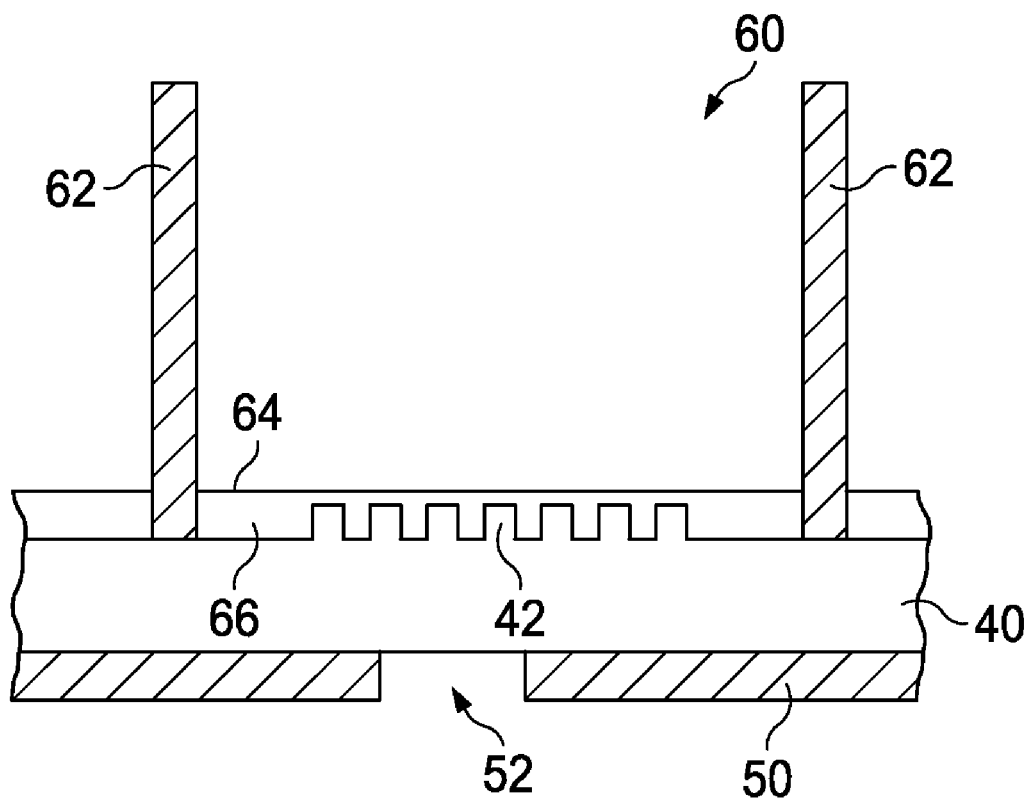
FIG. 6 is a partial cross section of a single well of the microplate of the present invention.

FIG. 6 is a partial cross sectional view of one well employing the aperture feature. A well 60 is defined by well walls 62 and well bottom 64. In the bottom of the well is an optical waveguide sensor comprising a substrate 40, a grating 42 and a waveguide layer 66. An opaque mask 52 is attached to the bottom surface of the substrate 40. An aperture 52 in the mask 50 allows optical access to the well 60 for any means of optical equipment. Signals can be launched and detected through the aperture 52. The mask material will preferably block all or selected forms of electromagnetic radiation both into and out of the system, depending on the application.

The mask material can be made of any material suitable for attachment to the substrate and suitable for blocking the transmitted light including organic or inorganic materials (e.g. metal, polymer, ceramic, etc.). Similarly and depending on the material, it may be attached to the bottom of the plate by any means (e.g. adhesive, chemical bonding, silk screening, etc.). It will also be appreciated that any means of providing a masking effect may be employed so long as an aperture of consistent size is created. For example, the blocking agent may itself be incorporated within the substrate. Alternatively the masking agent may be placed as a layer above waveguiding film or between the waveguiding layer and the grating, or between the substrate and the grating.

I claim:

1. A microplate comprising:
   a frame that forms sidewalls of a plurality of wells, the frame having a bottom surface that interconnects said wells;
   a first layer that forms a bottom of the plurality of wells, the layer having a top surface and a bottom surface, wherein said frame and said layer are attached such that said top surface of said layer contacts and bonds to said bottom surface of said frame;
   a plurality of waveguide grating based biosensors, each waveguide grating based biosensor is located within the bottom of each well; and
   a second layer comprising a mask attached to and in contact with the bottom surface of the first layer, said mask having a plurality of apertures that are aligned with the plurality of waveguide grating based biosensors, each aperture being smaller than a grating in each waveguide grating based biosensor, and wherein the mask is attached to the bottom surface of the first layer by an adhesive, a chemical bond, or a silk screen bond.

2. The microplate of claim 1 wherein said aperture is circular.

3. The microplate of claim 1 further comprising an array of 96 wells.

4. A method of interrogation comprising:
providing a microplate having a plurality of wells formed therein, where each well has a waveguide grating based biosensor in a bottom portion thereof and a mask attached to and in direct contact with the waveguide grating based biosensor, where the mask has an aperture that is aligned with the waveguide grating based biosensor, where the aperture is smaller than a grating in the waveguide grating based biosensor, and where the mask is attached to the waveguide grating based biosensor by an adhesive, a chemical bond, or a silk screen bond;
using a launch system to direct a light beam through the aperture toward the waveguide grating based biosensor, and wherein the light beam overfills the aperture in the mask; and
using a receive system to receive and interrogate the light beam that is reflected from the waveguide grating based biosensor.

5. The method of claim 4, wherein the width of said light beam is larger than a diameter of said aperture.

6. The method of claim 5, further comprising the step of using the launch system to direct another light beam through the aperture toward the waveguide grating based biosensor, where the aperture ensures that the another light beam hits a same region of the grating in the waveguide grating based biosensor as was done by the light beam during the first using step even when the microplate shifted relative to the launch system, where the width of the another light beam is larger than the diameter of said aperture.

7. A microplate comprising:
a frame that forms sidewalls of a plurality of wells, the frame having a bottom surface;
a layer that forms a bottom of the plurality of wells, the layer having a top surface and a bottom surface, wherein the frame and the layer are attached such that the top surface of the layer contacts and bonds to the bottom surface of the frame;
a plurality of waveguide grating based biosensors, each waveguide grating based biosensor is located within the bottom of each well; and
a mask in contact with and directly bonded to the bottom surface of the layer, the mask having a plurality of apertures that are aligned with the plurality of waveguide grating based biosensors, each aperture being smaller than a grating in each waveguide grating based biosensor, and wherein the mask is directly bonded to the bottom surface of the layer by an adhesive, a chemical bond, or a silk screen bond.

8. A microplate article comprising:
a plate having a plurality of parallel holes therethrough;
a base attached to a first face of the plate, the attached base creates a closed-end well from each hole;
a waveguide grating biosensor within each well on the base; and
a mask bonded to a face of the base opposite the attached plate, the mask having a light passable aperture aligned with each waveguide grating biosensor, and each light passable aperture having a facial area less than the facial area of the aligned grating, and wherein the mask is bonded to the face of the base opposite the attached plate by an adhesive, a chemical bond, or a silk screen bond.

9. The microplate article of claim 8 wherein the aperture comprises a pair of apertures.

10. An interrogation system for interrogating a microplate, the system comprising:
an optical source and receiver, the source emits an optical beam to the microplate and receives an optical beam from the microplate, the microplate comprises:
a frame that forms sidewalls of a plurality of wells, the frame having a bottom surface that interconnects the wells;
a first layer having a top surface and a bottom surface, the top surface is bonded to the bottom surface of the frame and seals one end of the wells;
at least one waveguide grating biosensor being located within at least one well; and
a second layer comprising a mask attached to and in contact with the bottom surface of the first layer, the mask having at least one aperture aligned with at least one waveguide grating biosensor, the aperture having a smaller area than the grating of the aligned waveguide grating biosensor, and the mask is attached to the first layer by an adhesive, a chemical bond, or a silk screen bond.

* * * * *